(12) United States Patent
DeLegge (10) Patent No.: US 7,883,525 B2
(45) Date of Patent: *Feb. 8, 2011

(54) INTRAGASTRIC CATHETER

(76) Inventor: Rebecca DeLegge, 2832 Stay Sail Way, Mt. Pleasant, SC (US) 29466

( * ) Notice: Subject to any disclaimer, the term of this patent is extended or adjusted under 35 U.S.C. 154(b) by 541 days.

This patent is subject to a terminal disclaimer.

(21) Appl. No.: 11/859,472

(22) Filed: Sep. 21, 2007

(65) Prior Publication Data

US 2008/0071305 A1    Mar. 20, 2008

Related U.S. Application Data

(63) Continuation-in-part of application No. 10/390,947, filed on Mar. 17, 2003, now Pat. No. 7,291,160.

(51) Int. Cl.
*A61M 29/02* (2006.01)

(52) U.S. Cl. ........................................ 606/192; 604/909

(58) Field of Classification Search .......... 606/191–199, 606/108; 604/96.01, 101.01–101.02, 103.05–103.08, 604/907, 909, 910
See application file for complete search history.

(56) References Cited

U.S. PATENT DOCUMENTS

| | | | |
|---|---|---|---|
| 4,501,264 A | 2/1985 | Rockey | |
| 4,648,383 A * | 3/1987 | Angelchik | 128/899 |
| 4,694,827 A | 9/1987 | Weiner et al. | |
| 4,739,758 A | 4/1988 | Lai et al. | |
| 4,787,388 A * | 11/1988 | Hofmann | 606/194 |
| 4,878,495 A | 11/1989 | Grayzel | |
| 5,234,454 A | 8/1993 | Bangs | |
| 5,379,759 A | 1/1995 | Sewell, Jr. | |
| 5,501,667 A * | 3/1996 | Verduin, Jr. | 604/101.01 |
| 5,725,535 A * | 3/1998 | Hegde et al. | 606/108 |
| 5,868,141 A | 2/1999 | Elias | |
| 5,947,924 A | 9/1999 | Liprie | |
| 5,954,739 A | 9/1999 | Bonutti | |
| 5,993,473 A * | 11/1999 | Chan et al. | 606/192 |
| 6,013,054 A | 1/2000 | Yan et al. | |
| 6,017,324 A | 1/2000 | Tu et al. | |
| 6,454,785 B2 | 9/2002 | Garza | |
| 6,746,460 B2 | 6/2004 | Gannoe et al. | |
| 7,056,305 B2 * | 6/2006 | Garza Alvarez | 604/191 |
| 7,264,631 B2 * | 9/2007 | DiCarlo | 623/1.11 |
| 2005/0159769 A1 | 7/2005 | Alverdy | |

FOREIGN PATENT DOCUMENTS

WO     WO 02/071951 A1     9/2002

\* cited by examiner

*Primary Examiner*—Anhtuan T Nguyen
*Assistant Examiner*—Elizabeth Houston
(74) *Attorney, Agent, or Firm*—B. Craig Killough (57) ABSTRACT

An intragastric catheter provides satiety due to its presence in the stomach cavity. Efficacy is improved by the tactile sensation provided by a plurality of fingers that extend from the device. Normal peristaltic action upon the device moves the fingers relative to the stomach. The structure of the intragastric catheter reduces the level of precision required in placement of the device, and blockage of conduits to and from the stomach by the device is unlikely.

12 Claims, 9 Drawing Sheets

INTRAGASTRIC CATHETER

CROSS-REFERENCE TO RELATED APPLICATION

This application is a Continuation-in-Part of U.S. application Ser. No. 10/390,947, filed Mar. 17, 2003, which is incorporated by reference.

BACKGROUND OF THE INVENTION

1. Field of the Invention

This invention relates to medical devices generally, and is more specifically related to an intragastric catheter that is useful in the treatment of obesity.

2. Description of Related Art

Morbid obesity is a major medical problem affecting millions of people. Many serious health problems are associated with morbid obesity, including hypertension, hyperlipidemia, exacerbation of diabetes mellitus, heart disease, degenerative arthritis, and Pickwickian syndrome, certain types of cancer, gallstones, varicose veins, thromboembolism and hernias. Additionally, morbid obesity can lead to psychosocial difficulties such as depression, loss of self-esteem and decreased employability.

Attempts to induce weight loss in morbidly obese patients have been largely unsuccessful. Diet, exercise and behavioral modification are usually not effective in the long term because the morbidly obese patient does not maintain adherence to these programs. Further, such programs may risk further damage to the patient's health. The long term use of pharmaceuticals in bariatric medicine is also problematic. Use of pharmaceutical agents may lead to addiction, undesired side effects, and/or loss of potency due to drug tolerance.

Surgical procedures that have been applied include jejunoileal or gastric bypass surgery, gastroplasty and gastric stapling and oral surgical procedures such as wiring shut the patient's jaws to reduce food intake. These procedures are effective in producing weight loss, but are invasive, with associated risks and recovery times, as well as being expensive and often ineffective over the long term.

Various intragastric inflatable balloon devices have been heretofore used. These devices occupy the stomach cavity, thereby reducing its volume, and providing satiety. Problems associated with these devices include undesired deflation, requiring surgical removal, and ulceration or necrosis created by constant pressure of the device on the stomach wall and gastric outlet obstruction.

Placement of devices by a percutaneous endoscopic gastrostomy (PEG) procedures, while less expensive than surgical procedures, are less precise. Balloon type intragastric catheters positioned by PEG procedures, as described in De Hoyos Garza, U.S. Pat. No. 6,454,785, may block only a portion of the stomach, or they may block entry to the stomach from the esophagus if the device is not precisely positioned.

SUMMARY OF THE PRESENT INVENTION

An intragastric catheter provides satiety due to its presence in the stomach cavity. Efficacy is improved by the tactile stimulation provided by a plurality of fingers that extend from the device. Normal peristaltic action upon the device moves the fingers relative to the stomach. The structure of the intragastric catheter reduces the level of precision required in placement of the device, and blockage of conduits to and from the stomach by the device is reduced.

DESCRIPTION OF THE PREFERRED EMBODIMENTS

Figure 1:
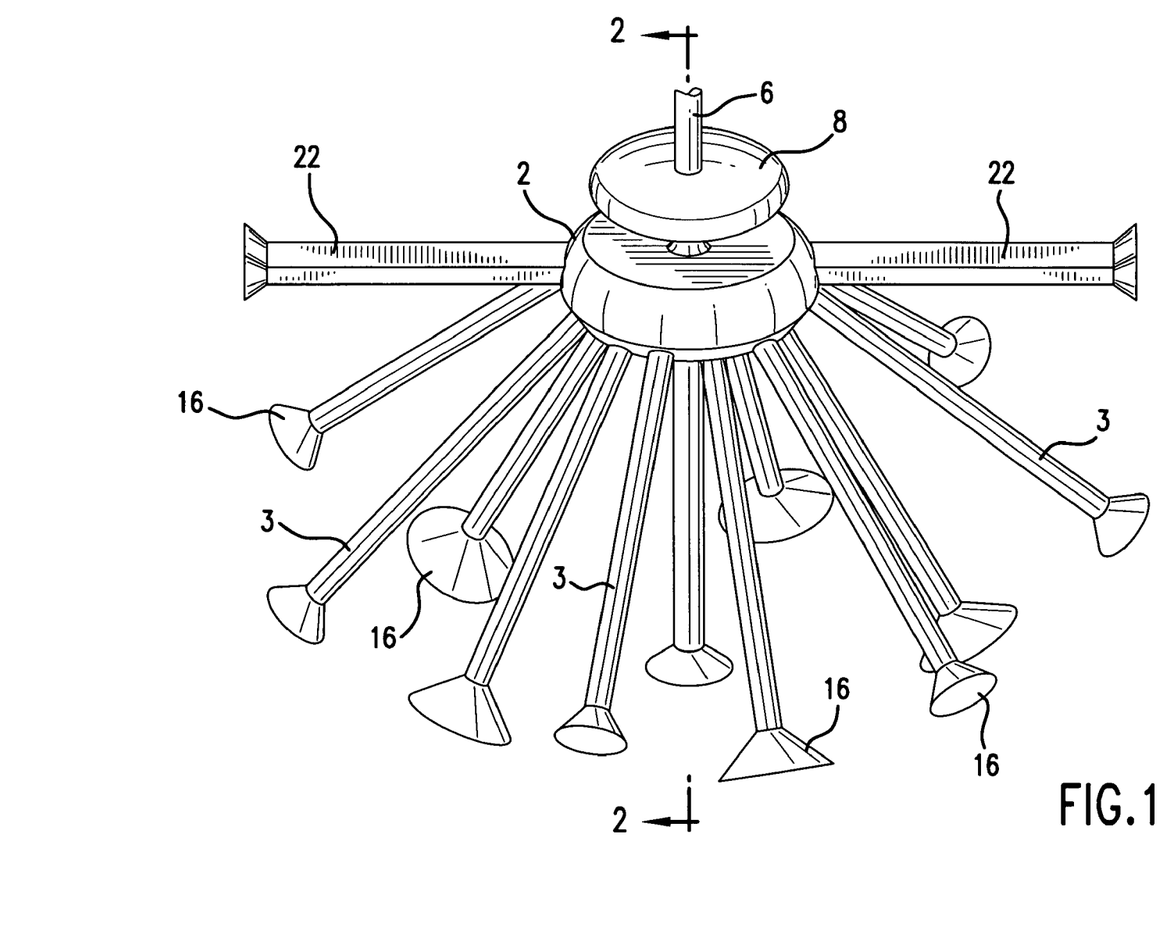
FIG. 1 is a perspective view of one embodiment of the intragastric catheter.

Referring now to FIG. 1, the intragastric catheter comprises a bladder 2. A plurality of finger-like tubules 3 extend from various locations on the lower surface of the bladder. In the embodiment as shown, a neck 4 connects a bolster to the bladder, and an external tube 6 extends percutaneously from the internal bolster 8, and communicates with an exterior of the stomach. External bolster 9 assists in holding the device in place within the stomach.

In a preferred embodiment, the bladder contains a fluid 10. The fluid may be a gas, a liquid, or a gel, or a mixture thereof, or a combination thereof. The fluid is provided to the bladder through external tube 6. Increasing or decreasing the volume and pressure of fluid that is present in the chamber variably inflates the bladder. The external tube 6 may have a cap 28 to help prevent the fluid from escaping, to help keep the entry to the external tube clean, and to provide a cover for a valve in the external tube.

In the preferred embodiment, the finger-like tubules are hollow, with the hollow space in the tubules communicating with the bladder to provide for a transfer of fluid. Accordingly, as the bladder is filled with fluid, the fluid flows into tubules, providing additional rigidity for the tubules, according to the volume and pressure of the fluid that is present in the chamber. The chamber acts as a reservoir to supply fluid to the tubules.

Figure 3:
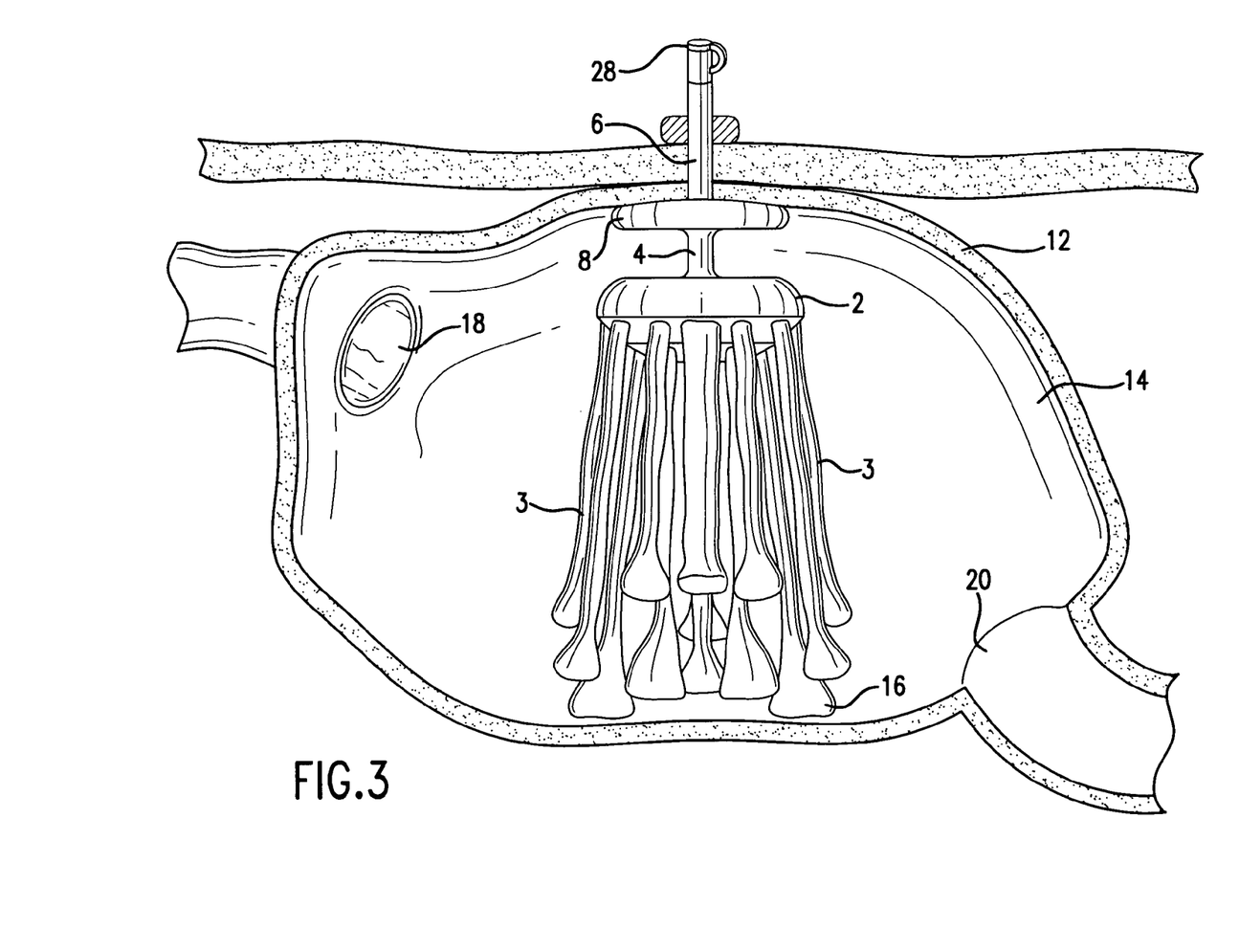
FIG. 3 is a side elevation of an intragastric catheter in the deflated state and positioned within a user's stomach.
Figure 4:
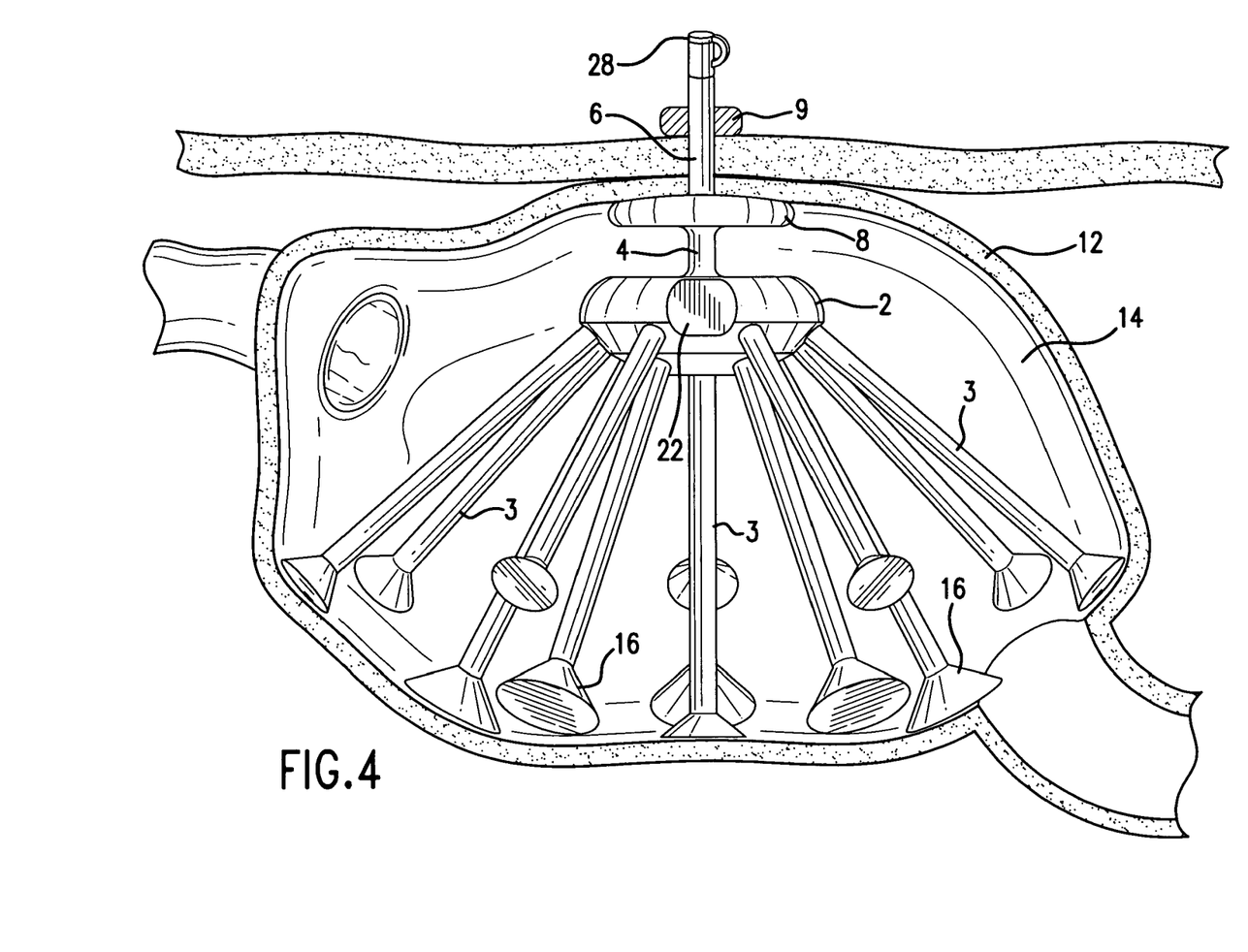
FIG. 4 is a side elevation of an intragastric catheter in the inflated state and positioned within a user's stomach.

The tubules are flexible, and are capable of a deformation relative to the bladder. Particularly at the point of attachment of the tubules to the bladder, the tubules may be displaced relative to the bladder. As normal peristaltic action of the stomach 14 causes the device to be moved about within the stomach, the ends of the tubules that are opposite the bladder are dynamic. Movement of the tubules from peristaltic action provides a tactile sensation against the wall of the stomach, which provides satiety. The tubules may be variably inflated by the device as required, to provide the desired tactile stimulation. If the tubules are substantially deflated, so that they are flaccid, as shown in FIG. 3, then little tactile stimulation will occur. On the other hand, over inflation may result in insufficient movement of the tubules. Movement of the tubules due to peristaltic action prevents the tubules from constantly contacting a single point of the stomach wall, thereby reducing necrosis or ulceration due to constant contact of the tubules with the stomach wall. In the preferred embodiment, the tubules have an enlarged end 16 that increases tactile stimulation. In the particular embodiment shown in the drawing figures, the enlarged end has a recess that is centrally disposed within the end. This recess in the end of the tubules helps reduce constant contact of the end of the tubules with the stomach wall by reducing the amount of surface area that comes in contact with the stomach wall.

Figure 5:
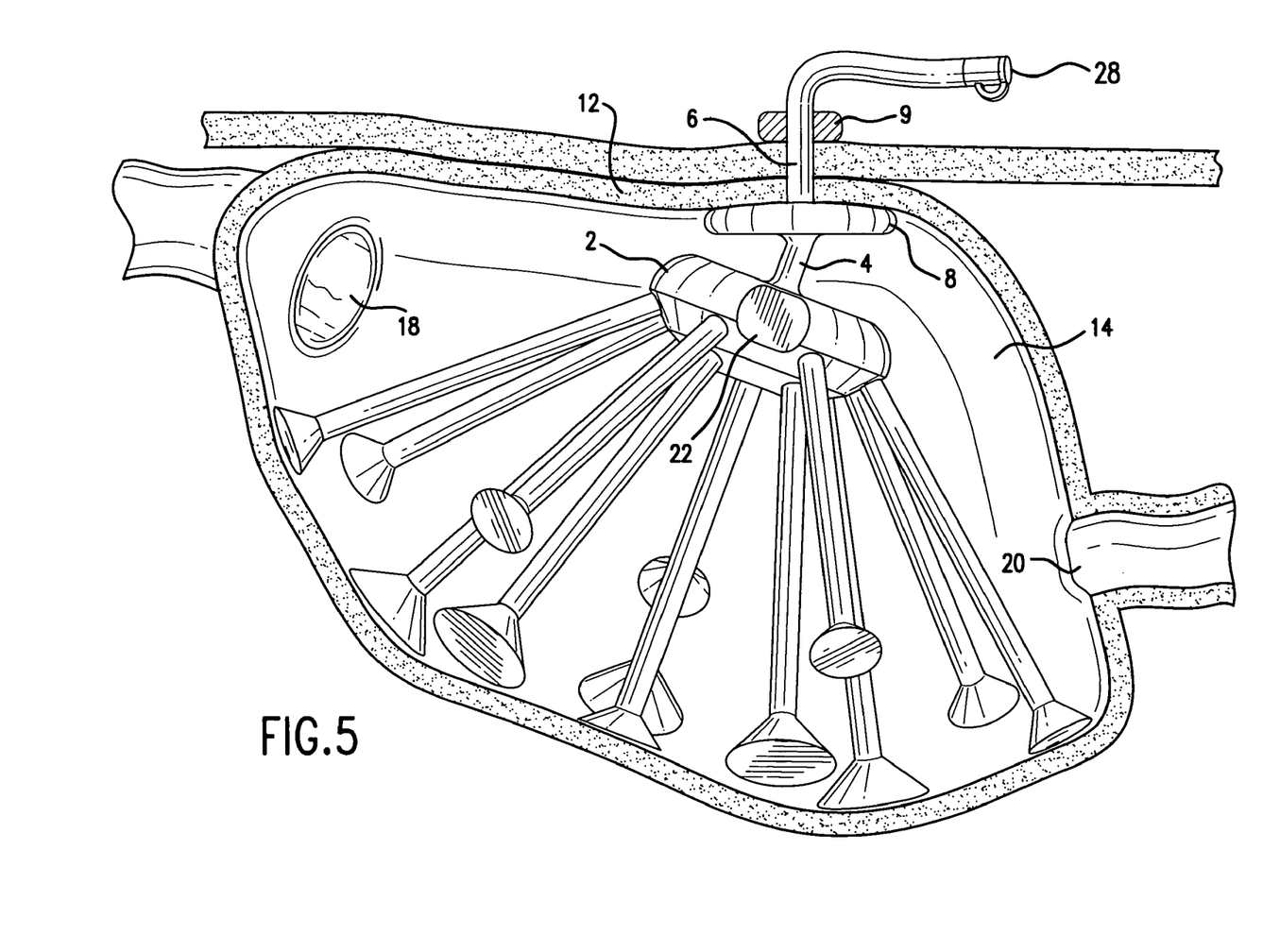
FIG. 5 is a side elevation of an intragastric catheter in the inflated state and positioned within a user's stomach.

The neck 4 of the device is deformable, which insures proper orientation of the device relative to the stomach. FIG. 5. The bolster 8 is adjacent to the stomach wall 12, while the deformable neck, which is present within the stomach, allows the remainder of the device to flex and bend relative to the bolster. Accordingly, if the device is positioned by a PEG procedure, and placement of the device is not optimal, the device deforms relative to bolster by means of the neck, so that the tubules contact the stomach wall. For example, if the placement is too high relative to optimal placement, the neck bends to allow the device to enter the relatively lower part of the stomach. The use of the finger like tubules, rather than a massive object like a balloon, prevents blockage of the entry 18 or exits 20 of the stomach.

Longer tubules 22 may be used to orient the device upon placement. As shown, tubules 22 from a higher point of the bladder when the device is positioned as in FIG. 1. Tubules 22 extend from the bladder and opposite each other, and are generally horizontally when inflated and when the device is positioned as shown in FIG. 1. These longer tubules help position the device. They are positioned by peristalsis and/or at placement so as to find the long axis of the stomach. If they are placed on the short axis, the stomach will move them to the position of least resistance. It is preferred that the device comprise at least three (3) tubules, although additional tubules may be used, as shown in the drawings.

In one embodiment of the invention, a valve is present where the tubule joins the bladder. The valve allows the tubule to be filled with fluid, but prevents fluid from returning to the chamber. In case of a leak in a particular tubule, the fluid will leak into the stomach from that tubule and it will become deflated. However, it is not necessary to replace the entire catheter as a result of the deflation of one, or a few, of the tubules, since the remainder of the device will remain inflated. The valves could be positioned within the tubules, near the end of the tubule that joins the bladder, or the valves could be positioned within the bladder near the entrance to the tubules.

Figure 2:
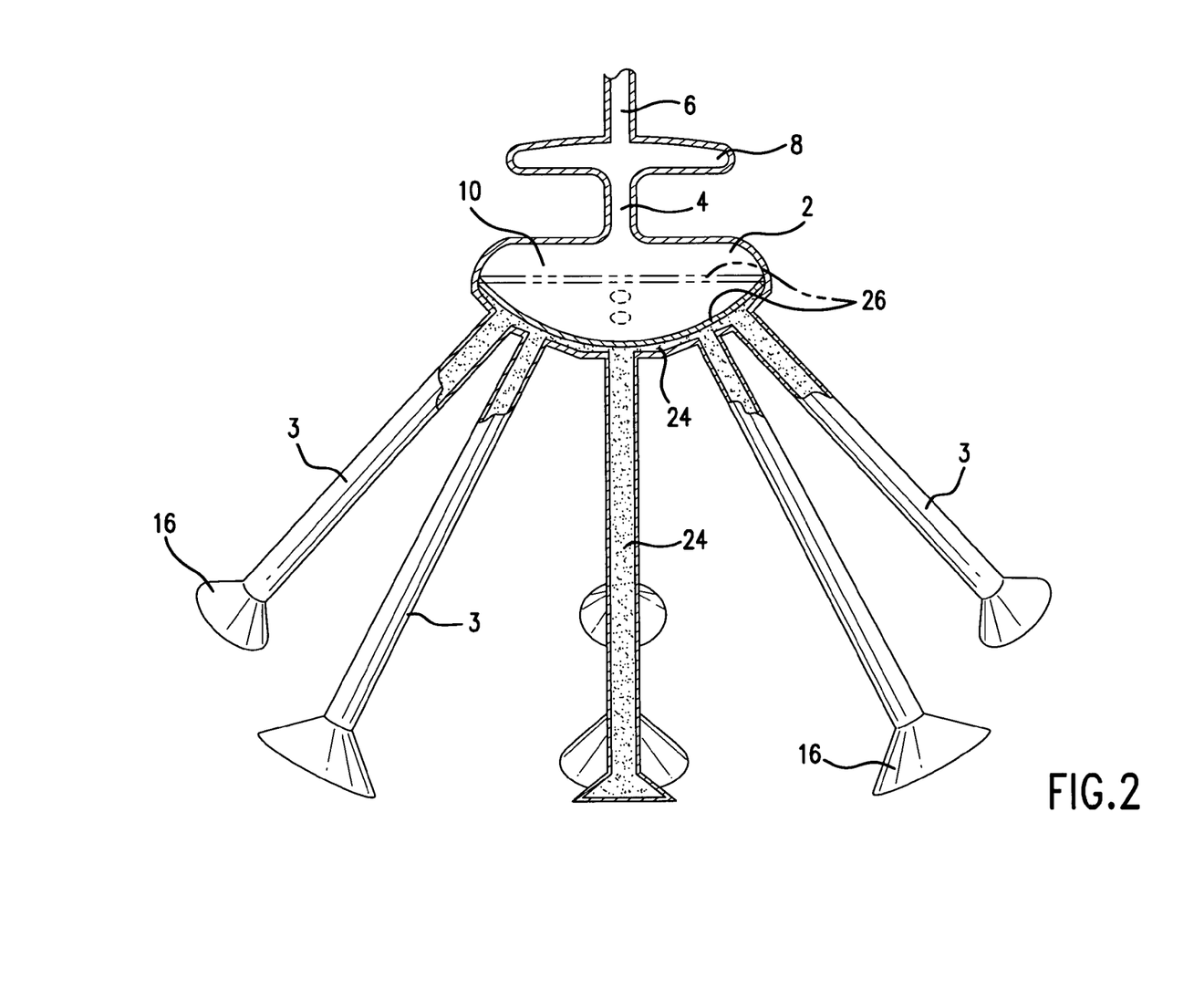
FIG. 2 is a sectioned view of the intragastric catheter, taken essentially along line 2-2 of FIG. 1.

In one embodiment of the bladder, a diaphragm 26 is present within the bladder. A fluid 24, which is preferred to be a liquid, a gel, or a mixture thereof, is present on one side of the diaphragm. This side of the diaphragm communicates with the tubules. A fluid 10 under pressure, which could be air, is present on the other side of the diaphragm, and is provided through the external tube. As the fluid pressure in the bladder is increased, the liquid pressure on the opposite side the diaphragm is increased, and the pressure and volume within the tubules is increased. While the use of the liquid or a gel to fill the tubules is preferred, handling and pressurizing a liquid or gel is more difficult for the patient, than is the application of air pressure. The patient may easily apply pressure to the device using an air pump, whereas attempting to pressurize a liquid or gel by the insertion of additional liquid or gel material under pressure is more difficult.

The device may be periodically inflated and deflated to simulate filling and emptying of the stomach with food. For example, the device may be inflated in conjunction with the consumption of a meal, so that less food is consumed by the user, while the stomach feels full. Alternatively, the device may be inflated in conjunction with the introduction of the smell of food, or other sensory inputs. The device may subsequently be deflated, including slow deflation, to simulate emptying of the stomach, although the device will still induce satiety by the movement of the tubules from peristaltic action.

The device may be constructed of suitable materials that will inflate or deflate when filled with a fluid. In a preferred embodiment, the device could be constructed of medical grade polyethylene terephthalate (PET). PET allows the device to have deformation characteristics similar to plastic storage bags that are commonly used in the kitchen, making it a suitable candidate for replacement by means of a percutaneous endoscopic gastrostomy (PEG) procedure as described herein. The tubules may be formed of two or more plies of material. For example, a 2-ply tubule will have better resistant to breakage or puncture than will a single ply tubule.

The intragastric catheter of the present invention may be introduced through the mouth, subsequently traveling through the esophagus and into the stomach. The abdominal wall is punctured, and a guide wire is inserted from the outside into the fundus of the stomach. The endoscope is grasped with the guide wire, and one end of the guide wire is extracted by pulling the endoscope out of the mouth while the other end of the guide wire remains outside of the abdomen. The intragastric catheter is placed through the abdominal wall by attaching the intragastric catheter to the guide wire extended out of the patient's mouth and pulling on the other end of the guide wire until the intragastric catheter is pulled through the puncture opening in the abdominal wall. The placed intragastric catheter is secured on the stomach wall with the bolster.

FIGS. 3 through 8 show the intragastric catheter as it is positioned intragastrically within the obese person. The intragastric catheter has multiple finger like tubules that extend from the bladder and are subject to the peristalsis within the stomach, which causes movement of the tubules to prevent pressure from being constantly applied on one surface of the stomach, and thereby preventing gastric erosion. The tactile sensation provided by the finger like tubules against the stomach provides satiety, and suppresses the patient's appetite. As shown in the drawing figures, the bladder is inflated to a size that is larger than the diameter of the esophagus, and is sufficiently large so that the bladder cannot pass through an esophagus of a user. The bladder, when filled with fluid, should contain not less than 20 milliliters of fluid.

Figure 6:
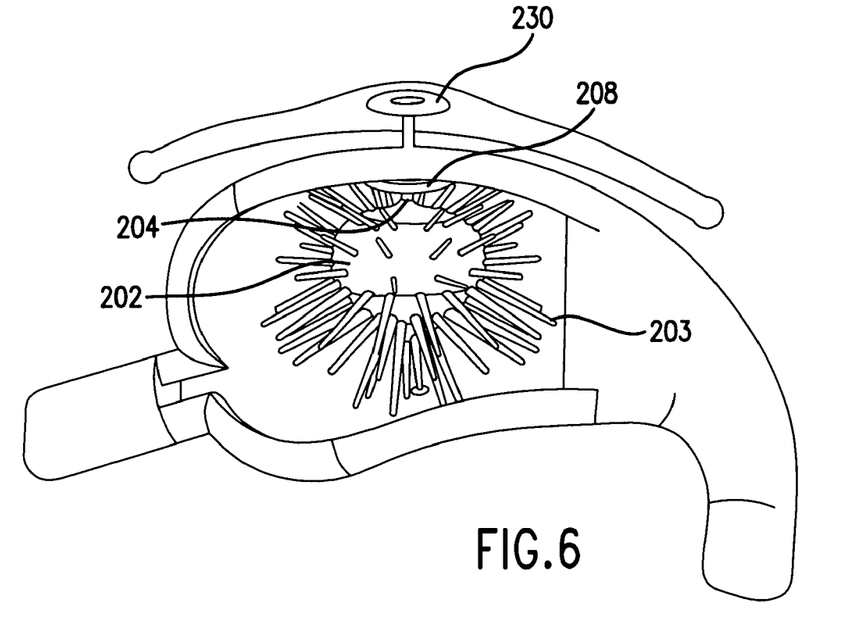
FIG. 6 shows an intragastric catheter in the inflated state and positioned within a user's stomach by subcutaneous attachment.
Figure 7:
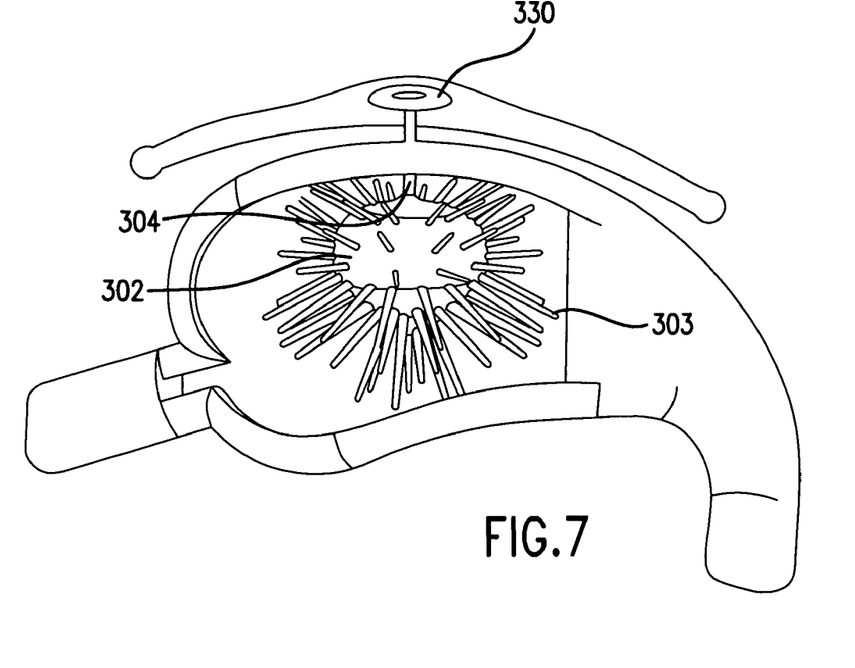
FIG. 7 shows another embodiment of an intragastric catheter in the inflated state and positioned within a user's stomach by subcutaneous attachment.

In one embodiment of the device demonstrated by FIGS. 6 and 7, the intragastric catheter is positioned subcutaneously. This embodiment may or may not be positioned by percutaneous methods. An attachment point 230,330 is provided that may be on one end of the neck. The attachment point may be opposite the bladder and the tubules, and connected to the bladder 202,302 by a neck 204,304. The attachment point is positioned below the skin, and the skin heals over the attachment point. The risk of infection is decreased by the skin covering the attachment point. The attachment point may be connected by a fastener, which may be a T connector, or suture material, or other known fasteners or other devices for attaching a medical device to tissue.

The neck is deformable, and flexes or pivots relative to the attachment point, or if used, relative to the bolster. The attached bladder moves by peristaltic action and/or gravity, with the elongated finger like tubules 203,303 providing tactile stimulation to the stomach. The neck permits movement of the bladder within the stomach, while connecting the bladder to the attachment point that keeps the device attached and anchored.

A bolster 208 may be provided in one embodiment. The bolster is positioned within the stomach cavity, and restricts movement of the bladder above the bolster. The bolster may be positioned against the stomach wall. The bolster contacts the stomach wall at least during movement of the bladder, as the bladder and tubules move according to the teaching herein. The bolster reduces the possibility of the intragastric catheter breaking loose due to movement of the bladder relative to the attachment point.

Figure 8:
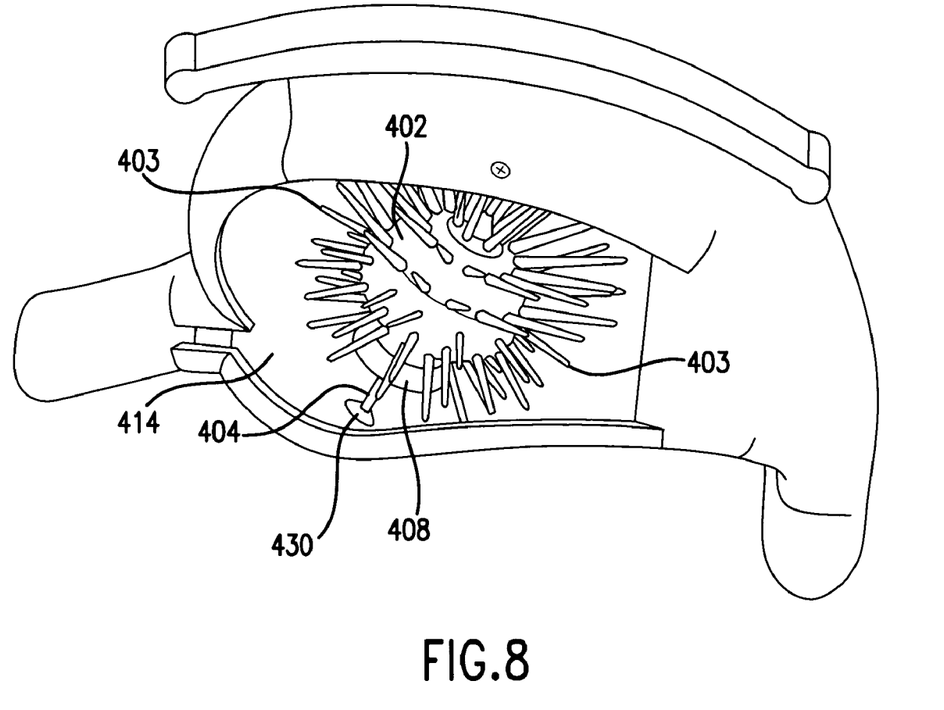
FIG. 8 shows an intragastric catheter in the inflated state and positioned within a user's stomach by attachment to stomach tissue.
Figure 9:
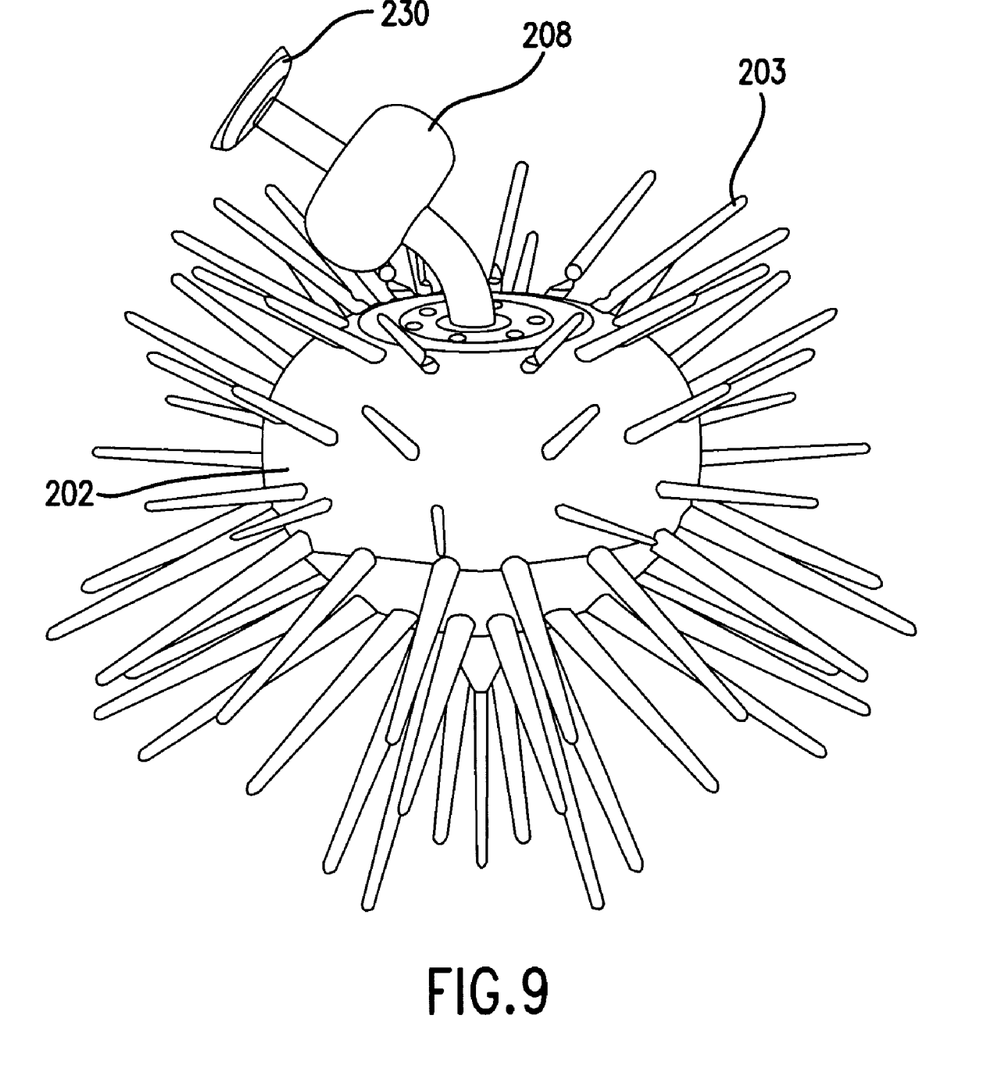
FIG. 9 is a perspective view of an embodiment of the intragastric catheter.
Figure 10:
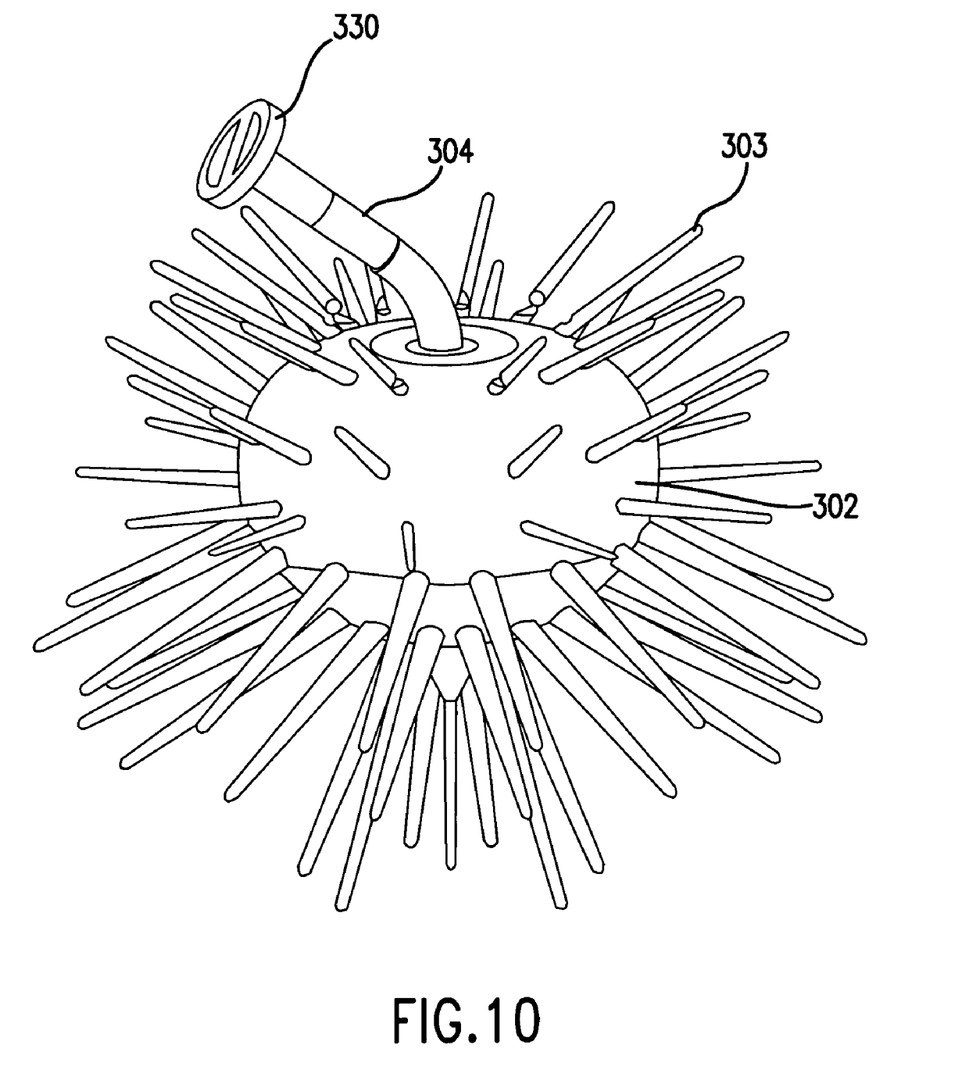
FIG. 10 is a perspective view of an embodiment of the intragastric catheter.

In one embodiment of the device, demonstrated by FIG. 8, the intragastric catheter is attached to tissue surrounding the device, such as by attachment to the interior of the stomach 414 or other internal tissue structures. This embodiment may or may not be positioned by percutaneous methods. An attachment point is provided 430 that may be on one end of the neck and opposite the bladder. The attachment point may be opposite the bladder and the tubules and connected to the bladder 402 by a neck 404. The neck is deformable, and flexes or pivots relative to the attachment point. The attached bladder moves by peristaltic action and/or gravity, with the elongated finger like tubules 403 providing tactile stimulation to the stomach. The neck permits movement of the bladder within the stomach, while connecting the bladder to the attachment point that keeps the device attached and anchored. A bolster 408 may be provided. The attachment point may be connected to the stomach tissue or other tissue by a fastener, which may be a T connector, or suture material, or other known fasteners or other devices for attaching a medical device to tissue.

What is claimed is:

1. An intragastric catheter for placement in a stomach to provide satiety, comprising:
   a bladder;
   a plurality of elongated flexible tubules, each of the plurality of elongated flexible tubules having a length that exceeds a width, and each of the plurality of elongated flexible tubules extend lengthwise and radially from the bladder, wherein the plurality of elongated flexible tubules comprises more than two elongated flexible tubules;
   and a flexible neck that is positioned between the bladder and an attachment point, wherein the bladder is so constructed and arranged for movement within the stomach by peristaltic action of the stomach on the bladder that flexes the flexible neck relative to the attachment point, and the elongated flexible tubules are so constructed and arranged for flexing relative to said bladder by contact with the stomach from peristaltic action within the stomach, and wherein the bladder has a different shape than the elongated flexible tubules.

2. An intragastric catheter, as described in claim 1, wherein said bladder and said more than two elongated flexible tubules are inflatable.

3. An intragastric catheter as described in claim 1, wherein said more than two elongated flexible tubules comprise a fluid therein.

4. An intragastric catheter as described in claim 1, wherein each of said of more than two elongated flexible tubules communicates with said bladder, and said plurality of tubules are formed to receive fluid from said bladder.

5. An intragastric catheter as described in claim 1, wherein each of said of more than two elongated flexible tubules has an enlarged distal end that is opposite a proximate end of each of said more than two elongated flexible tubules that is adjacent to said bladder.

6. An intragastric catheter as described in claim 1, wherein said more than two elongated flexible tubules comprises at least four elongated flexible tubules.

7. An intragastric catheter as described in claim 1, wherein the intragastric catheter is constructed and arranged such that a distance from the attachment point to a distal end of each of the elongated flexible tubules that is opposite the bladder is sufficient so that the distal end of each of the elongated flexible tubules are adapted to contact the stomach and movement of the elongated flexible tubules is not impeded by the stomach.

8. An intragastric as described in claim 1, wherein the intragastric catheter is adapted to be fixed to tissue of a user at the attachment point by a fastener.

9. An intragastric catheter as described in claim 1, wherein the bladder comprises a fluid under pressure that expands the bladder.

10. An intragastric catheter, as described in claim 1, wherein said bladder and said more than two elongated flexible tubules are deflatable.

11. An intragastric catheter as described in claim 1, wherein the bladder comprises a fluid under pressure that expands the bladder and wherein fluid is contained in said bladder in a volume that is not less than 20 milliliters.

12. An intragastric catheter as described in claim 1, wherein, when fluid is not present in the bladder, said bladder is of a size that the bladder is adapted to pass through an esophagus of an adult human, and upon inflation by the bladder comprising fluid under pressure, the bladder is expanded to a size that said bladder is adapted to pass through an esophagus of an adult human.

* * * * *